(12) United States Patent
Joshi et al.

(10) Patent No.: US 9,086,360 B2
(45) Date of Patent: Jul. 21, 2015

(54) METHOD AND APPARATUS FOR THERMAL CONTROL IN A CT DETECTOR

(71) Applicant: General Electric Company, Schenectady, NY (US)

(72) Inventors: Ashutosh Joshi, Waukesha, WI (US); Joseph Lacey, Cambridge, WI (US)

(73) Assignee: General Electric Company, Schenectady, NY (US)

( * ) Notice: Subject to any disclaimer, the term of this patent is extended or adjusted under 35 U.S.C. 154(b) by 98 days.

(21) Appl. No.: 13/916,074

(22) Filed: Jun. 12, 2013

(65) Prior Publication Data

US 2014/0369461 A1    Dec. 18, 2014

(51) Int. Cl.
*A61B 6/00* (2006.01)
*G01N 23/083* (2006.01)
*A61B 6/03* (2006.01)

(52) U.S. Cl.
CPC .............. *G01N 23/083* (2013.01); *A61B 6/032* (2013.01); *A61B 6/4233* (2013.01); *A61B 6/4488* (2013.01); *A61B 6/482* (2013.01)

(58) Field of Classification Search
CPC ........ A61B 6/032; A61B 6/42; A61B 6/4488; G01N 23/046

USPC ........... 378/4–20, 98.8, 199, 200; 250/370.15
See application file for complete search history.

(56) References Cited

U.S. PATENT DOCUMENTS

| | | |
|---|---|---|
| 6,931,092 B2 | 8/2005 | Joshi et al. |
| 7,062,008 B2 | 6/2006 | Joshi et al. |
| 7,065,173 B2 | 6/2006 | Lacey et al. |
| 7,102,308 B2 | 9/2006 | Lacey et al. |
| 7,236,562 B2 | 6/2007 | Joshi et al. |
| 7,512,209 B2 | 3/2009 | Joshi et al. |
| 2005/0117698 A1* | 6/2005 | Lacey et al. ..................... 378/19 |
| 2006/0109956 A1* | 5/2006 | Lacey .......................... 378/199 |
| 2012/0177174 A1 | 7/2012 | Ikhlef et al. |
| 2012/0183119 A1 | 7/2012 | Ikhlef et al. |
| 2012/0321041 A1 | 12/2012 | Ikhlef et al. |
| 2013/0037251 A1 | 2/2013 | Joshi et al. |

* cited by examiner

*Primary Examiner* — Courtney Thomas
(74) *Attorney, Agent, or Firm* — Lucas Divine; General Electric Company

(57) ABSTRACT

A CT system includes a rotatable gantry having an opening for receiving an object to be scanned, an x-ray source configured to project x-rays through the opening, and a detector assembly positioned to receive the x-rays. The detector assembly includes a plurality of readout chips positioned within a cooling zone and configured to receive electrical signals from a plurality of diode arrays, and a fan positioned to blow air into the cooling zone. An air temperature within the cooling zone is controlled independent of a speed of the fan.

12 Claims, 6 Drawing Sheets

METHOD AND APPARATUS FOR THERMAL CONTROL IN A CT DETECTOR

BACKGROUND

This disclosure relates generally to diagnostic imaging and, more particularly, to temperature control in a detector for a computed tomography (CT) gantry.

Typically, in computed tomography (CT) imaging systems, an x-ray source emits a fan or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are transmitted to the data processing system via A/D ASICs for image reconstruction. Imaging data may be obtained using x-rays that are generated at a single polychromatic energy. However, some systems may obtain multi-energy images that provide additional information for generating images.

Components within the detector, to include the scintillator, the photodiodes, and the A/D ASIC, are temperature sensitive and are typically calibrated during system calibration. Thus, it is desirable to perform system calibration at the operating temperature of the system to avoid image quality issues that may arise if the temperature in these components drifts during system use. It is also therefore desirable to maintain the environment within the gantry at a controlled temperature to minimize thermal drift during use.

CT gantries are therefore typically air cooled, but may be operated in rooms that range in temperature from 18° C. to 26° C. Usage of the CT system can widely vary as well, resulting in the gantry air ranging in temperature from 18° C. to greater than 35° C. Thus there are widely varying temperatures that may be experienced within the gantry (caused by heavy or light usage of the x-ray tube and other components), and the ability to design systems that cool and control the inner gantry temperature may be further compounded because of the widely varying ambient temperatures that may be experienced.

To provide generally constant component temperature operation, some CT detector systems include a heater that is attached to the detector. A sensor on the detector and/or its components thus may be used as input to a heater controller, enabling a generally uniform temperature of the components to be achieved during calibration and during system operation. That is, the detector can be heated above the maximum gantry inner air temperature and, in conjunction with the gantry ambient airflow, detector component temperature uniformity can generally be obtained.

However, in recent years the A/D ASICs (which are a heat source) and other electronic components (i.e., on a DAS) have been moved closer to the photodiodes in an effort to improve signal-noise ratio in CT detectors. Although the signal-noise ratio may be improved, moving the heat source(s) closer to the detector components can also compromise the ability to globally and uniformly cool the detector within the gantry using the general environment within the gantry. As such, some system designs include a heat sink material that is placed in thermal contact with the ASICs and other heat sources on detector modules, and the heat sink materials are convectively cooled. That is, a CT system may include numerous detector modules, each of which includes a DAS card that is positioned in close thermal proximity to the photodiode array. The DAS card includes the ASIC(s) which are directly cooled via the heat sink and the convective air blown over them. Typically as well, the individual DAS/heat sink modules may be placed within a plenum through which air is blown, using fans that are directly coupled to the plenum. Heat generated in the DAS components is thereby convectively cooled, and heat transfer to the thermally sensitive components is thus controlled.

The plenum for cooling numerous DAS cards may include a plurality of fans, five in one example. Each fan therefore may provide convective flow for its own "zone" that may include 10-12 DAS cards, as one example. Further, thermal gradients may also develop between zones, each of which may experience very different thermal conditions due to geometric effects within the gantry. That is, the leading zone in the rotational direction may experience convective airflow fed to it fan, while the central or trailing zones may experience different amounts of available airflow.

Thus, given the widely varying ambient conditions, system operating conditions, and the geometric effects, fan speed for each zone is separately controlled. Fan speed is therefore cycled through a wide range of operating speeds during system use. However, individual zone control of the fans can cause crosstalk between zones within the plenum, and air blown in one zone can affect airflow in neighboring zone(s). Fan cycling can also lead to early life failure of the fan, leading to costly repairs. Fan cycling can also cause an increase in acoustic noise as the bearing in the fan ages. In fact, fan cycling itself can appear as a nuisance to a system user who, hearing the fan cycling, may suspect imminent failure of the fan or be simply annoyed by the cycling.

Therefore, it would be desirable to have a method and apparatus to improve thermal performance within a CT gantry.

BRIEF DESCRIPTION

Embodiments are directed toward a method and apparatus for temperature control in a detector for a computed tomography (CT) gantry.

According to one aspect, a CT system includes a rotatable gantry having an opening for receiving an object to be scanned, an x-ray source configured to project x-rays through the opening, and a detector assembly positioned to receive the x-rays. The detector assembly includes a plurality of readout chips positioned within a cooling zone and configured to receive electrical signals from a plurality of diode arrays, and a fan positioned to blow air into the cooling zone. An air temperature within the cooling zone is controlled independent of a speed of the fan.

According to another aspect, a method of cooling detector electronics within an imaging gantry includes blowing air with a fan into a cooling zone in which the detector electronics are positioned, and controlling a temperature of the detector electronics without altering a speed of the fan.

According to yet another aspect, a detector assembly is positionable to receive x-rays from an x-ray tube within an imaging system. The detector assembly includes a cooling zone having a plurality of readout chips positioned therein, the readout chips configured to receive electrical signals from a plurality of diode arrays, and a fan coupled to the detector assembly and positioned to blow air into the cooling zone. An air temperature within the cooling zone is controlled independent of a speed of the fan.

Various other features and advantages will be made apparent from the following detailed description and the drawings.

DETAILED DESCRIPTION

The operating environment of disclosed embodiments is described with respect to a sixty-four-slice computed tomography (CT) system. However, it will be appreciated by those skilled in the art that embodiments of the disclosed subject matter are equally applicable for use with other multi-slice configurations. Moreover, disclosed embodiments will be described with respect to the detection and conversion of x-rays. However, one skilled in the art will further appreciate that embodiments are equally applicable for the detection and conversion of other high frequency electromagnetic energy. Disclosed embodiments will be described with respect to a "third generation" CT scanner, but is equally applicable with other CT systems as well as vascular and surgical C-arm systems and other x-ray tomography systems.

Figure 1:
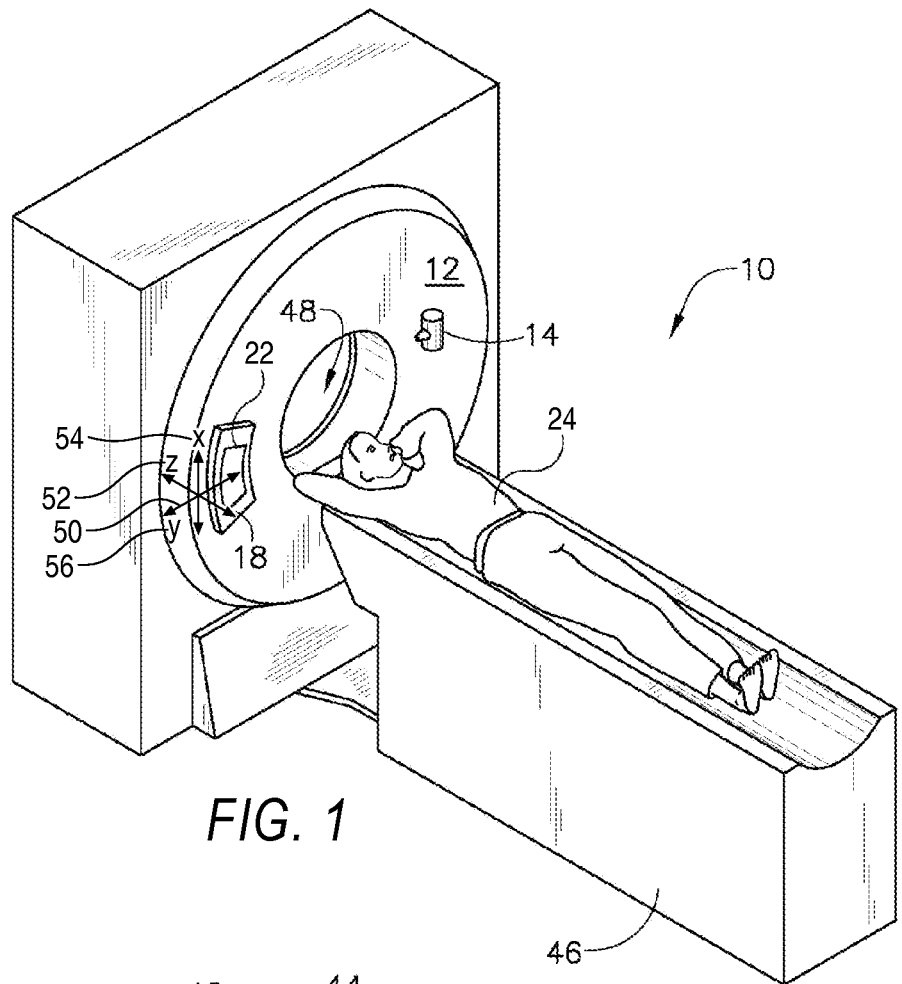
FIG. 1 is a pictorial view of a CT imaging system that incorporates embodiments of the disclosed subject matter.
Figure 2:
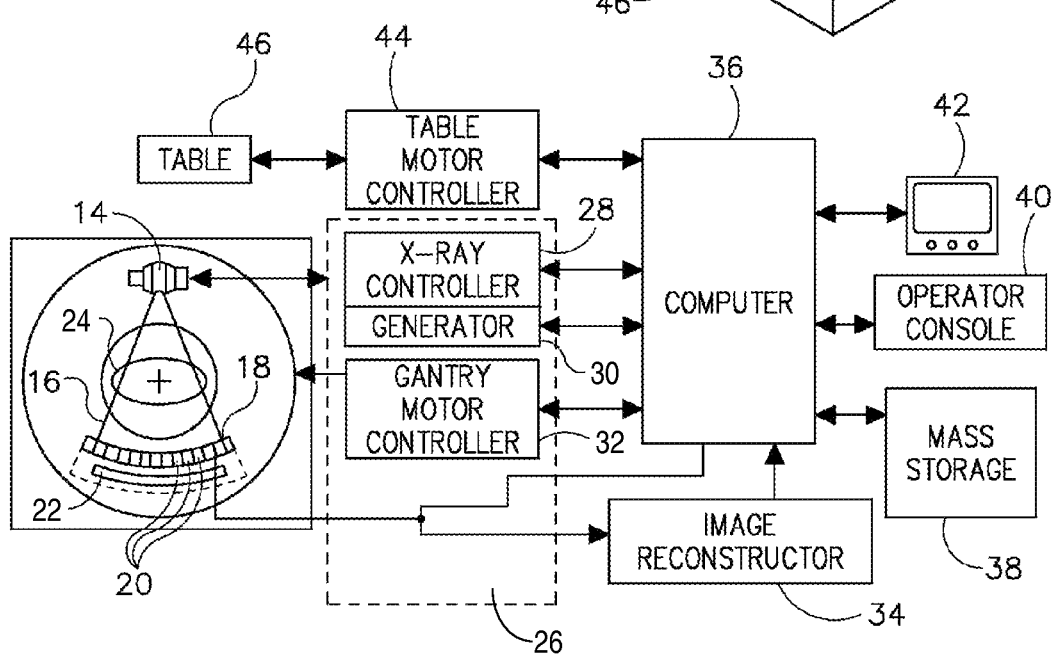
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray tube or source 14 that projects a beam of x-rays 16 toward a detector assembly or collimator 18 on the opposite side of the gantry 12. X-ray source 14 includes either a stationary target or a rotating target. Detector assembly 18 is formed by a plurality of detectors 20 and data acquisition systems (DAS) 22. The plurality of detectors 20 sense the projected x-rays that pass through a medical patient 24, and DAS 22 converts the data to digital signals for subsequent processing. Each detector 20 produces an analog electrical signal that represents the intensity of an impinging x-ray beam and hence the attenuated beam as it passes through patient 24. During a scan to acquire x-ray projection data, gantry 12 and the components mounted thereon rotate about a center of rotation.

Rotation of gantry 12 and the operation of x-ray source 14 are governed by a control mechanism 26 of CT system 10. Control mechanism 26 includes an x-ray controller 28 and generator 30 that provides power and timing signals to x-ray source 14 and a gantry motor controller 32 that controls the rotational speed and position of gantry 12. An image reconstructor 34 receives sampled and digitized x-ray data from DAS 22 and performs high speed image reconstruction. The reconstructed image is applied as an input to a computer 36 which stores the image in a mass storage device 38.

Computer 36 also receives commands and scanning parameters from an operator via an operator console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 22, x-ray controller 28, and gantry motor controller 32. In addition, computer 36 operates a table motor controller 44 which controls a motorized table 46 to position patient 24 and gantry 12. Particularly, table 46 moves patient 24 through a gantry opening 48 in whole or in part. A coordinate system 50 for detector assembly 18 defines a patient or Z-axis 52 along which patient 24 is moved in and out of opening 48, a gantry circumferential or X-axis 54 along which detector assembly 18 passes, and a Y-axis 56 that passes along a direction from a focal spot of X-ray source 14 to detector assembly 18.

X-ray source 14, in accordance with present embodiments, is configured to emit x-rays 16 at one or more energies. For example, x-ray source 14 may be configured to switch between relatively low energy polychromatic emission spectra (e.g., at approximately 80 kVp) and relatively high energy polychromatic emission spectra (e.g., at approximately 140 kVp). As will be appreciated, x-ray source 14 may also be operated so as to emit x-rays at more than two different energies. Similarly, x-ray source 14 may emit at polychromatic spectra localized around energy levels (i.e., kVp ranges) other than those listed herein (e.g., 100 kVP, 120 kVP, etc.). Selection of the respective energy levels for emission may be based, at least in part, on the anatomy being imaged.

In some embodiments X-ray controller 28 may be configured to selectively activate x-ray source 14 such that tubes or emitters at different locations within system 10 may be operated in synchrony with one another or independent of one another. In certain embodiments discussed herein, the x-ray controller 28 may be configured to provide fast-kVp switching of x-ray source 14 so as to rapidly switch source 14 to emit X-rays at the respective polychromatic energy spectra in succession during an image acquisition session. For example, in a dual-energy imaging context, x-ray controller 28 may operate x-ray source 14 so that x-ray source 14 alternately emits x-rays at the two polychromatic energy spectra of interest, such that adjacent projections are acquired at different energies (i.e., a first projection is acquired at high energy, the second projection is acquired at low energy, the third projection is acquired at high energy, and so forth). In one such implementation, fast-kVp switching operation performed by x-ray controller 28 yields temporally registered projection data. In some embodiments, other modes of data acquisition and processing may be utilized. For example, a low pitch helical mode, rotate-rotate axial mode, N×M mode (e.g., N low-kVp views and M high-kVP views) may be utilized to acquire dual-energy datasets.

Figure 3:
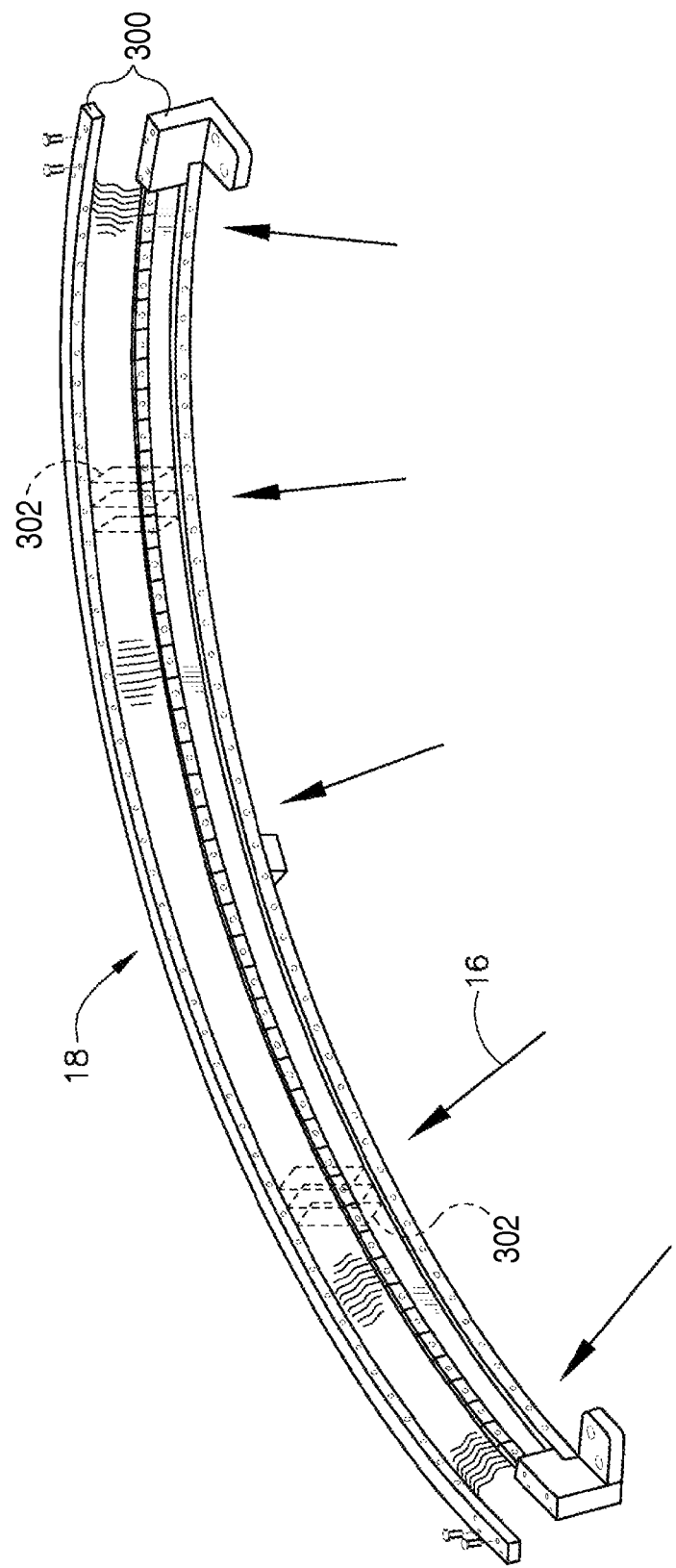
FIG. 3 is a perspective view of one embodiment of a CT system detector array.

As shown in FIG. 3, detector assembly 18 includes rails 300 having collimating blades or plates 302 placed therebetween. Plates 302 are positioned to collimate x-rays 16 before such beams impinge upon, for instance, detector 20 of FIG. 4 positioned on detector assembly 18. In one embodiment, detector assembly 18 includes fifty-seven detectors 20, each detector 20 having an array size of 64×16 of pixel elements 400. As a result, detector assembly 18 has sixty-four rows and nine hundred twelve columns (16×57 detectors) which allows sixty-four simultaneous slices of data to be collected with each rotation of gantry 12.

Figure 4:
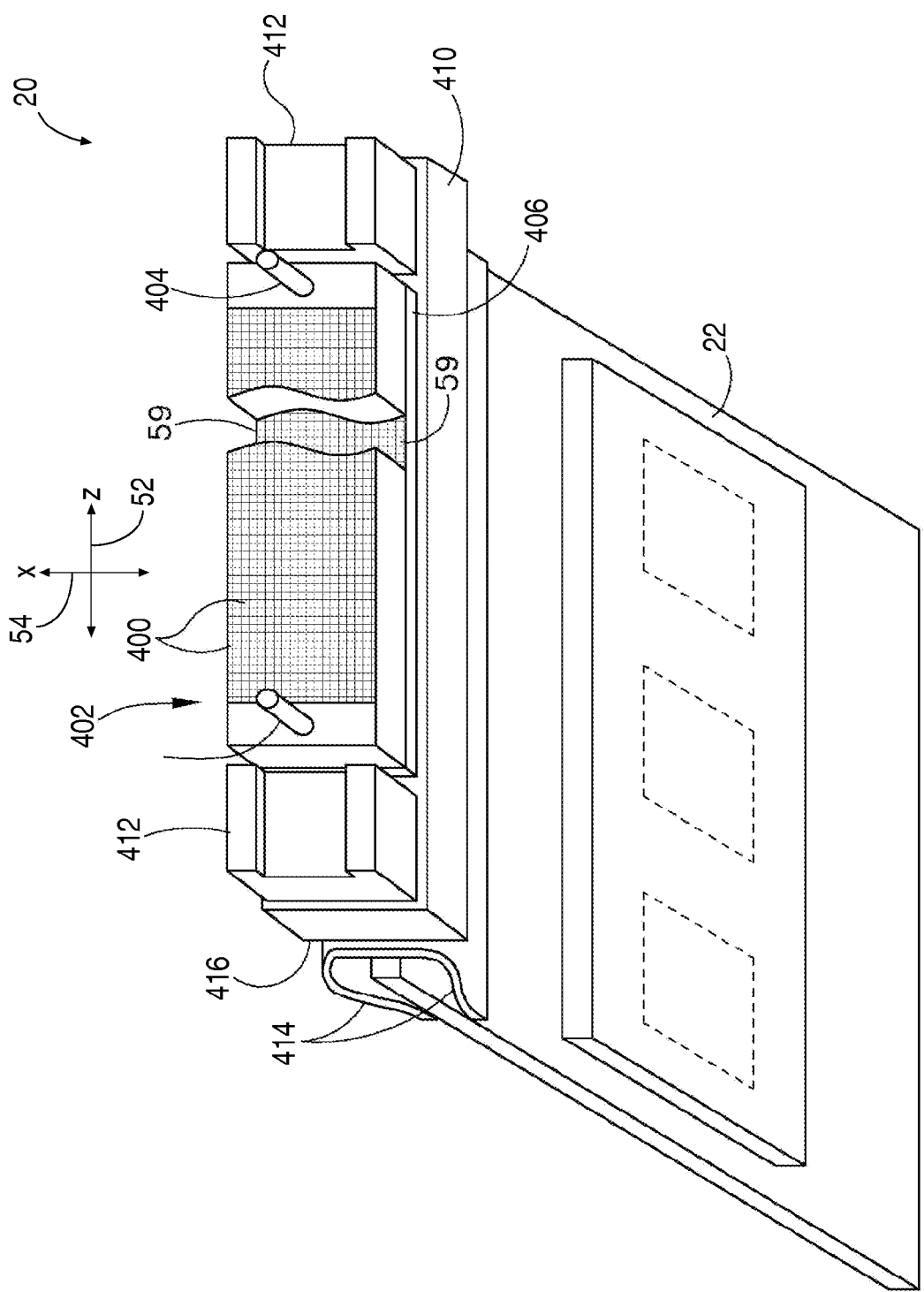
FIG. 4 is a perspective view of one embodiment of a detector.

Referring to FIG. 4, detector 20 includes DAS 22, with each detector 20 including a number of detector elements 400 arranged in pack 402. Detectors 20 include pins 404 positioned within pack 402 relative to detector elements 400. Pack 402 is positioned on a backlit diode array 406 having a plurality of diodes 408. Backlit diode array 406 is in turn positioned on multi-layer substrate 410. Spacers 412 are positioned on multi-layer substrate 410. Detector elements 400 are optically coupled to backlit diode array 406, and backlit diode array 406 is in turn electrically coupled to multi-layer substrate 410. Flex circuits 414 are attached to face 416 of multi-layer substrate 410 and to DAS 22. Detectors 20 are positioned within detector assembly 18 by use of pins 404.

Figure 5A:
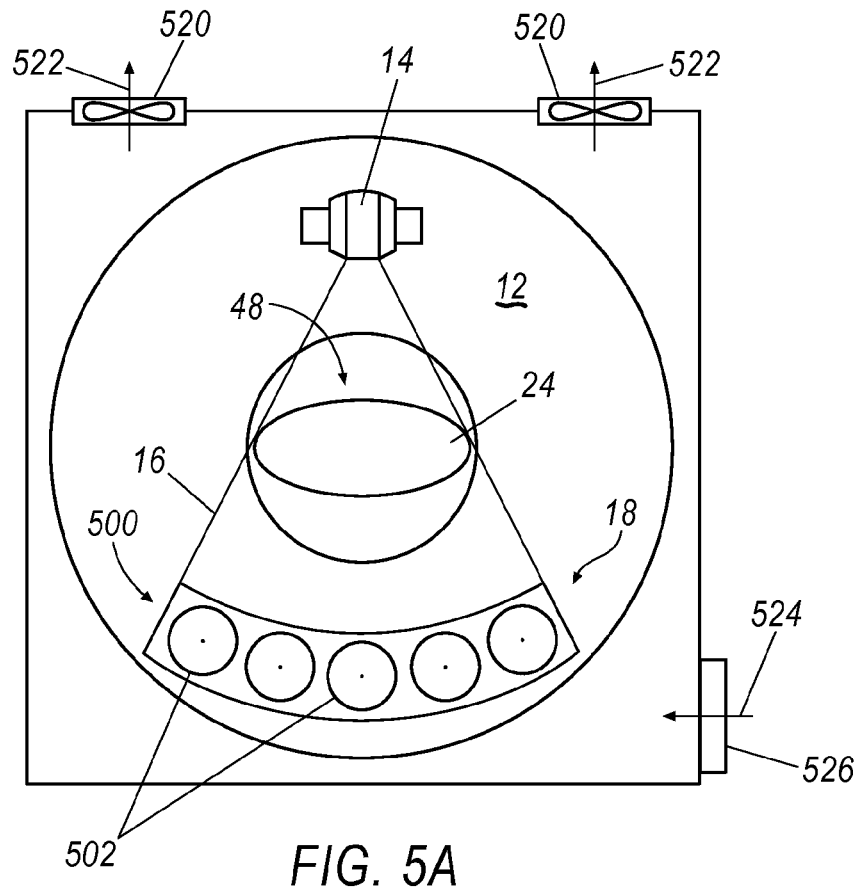
FIG. 5A is a plan view of a gantry having cooling zones and fans.

Referring to FIG. 5A, a plan view of a CT gantry is shown that incorporates embodiments of the disclosed subject matter. Consistent with that shown in FIGS. 1 and 2, gantry 12 includes x-ray source 14 that generates x-rays 16 that pass through gantry opening 48 and through object 24. Detector assembly 18 includes a plurality of detector modules (not shown) that are positioned within a cooling plenum 500. Detector assembly 18 includes detector electronics that include a plurality of readout chips configured to receive electrical signals from a plurality of diode arrays that are activated when impinged with the x-rays. Cooling plenum 500 includes a plurality of openings and fans 502, five in the illustrated embodiment, which are configured to blow air through respective cooling zones in which the detector modules are positioned.

Figure 5B:
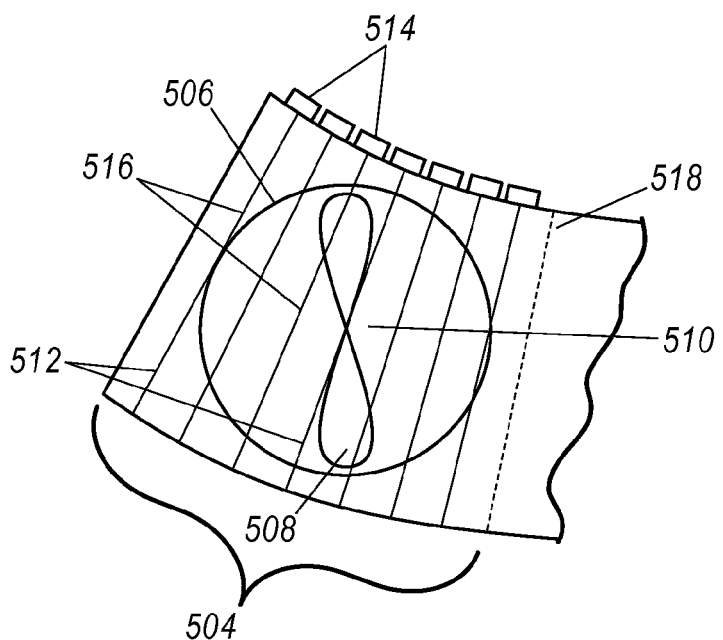
FIG. 5B is a plan view of a single cooling zone for multiple detector modules.

FIG. 5B includes a cooling zone 504 within plenum 500 of FIG. 5A, having an opening 506, which is one of openings 502. Opening 506 includes a fan 508 that is operated by a motor 510 that is positioned at its center. Cooling zone 504 represents one of several cooling zones, each of which includes a plurality of detectors 512, such as detector 20 of FIG. 4. Each detector 512 includes a detector front end 514 that may include a scintillator pack, readout diode array (front or backlit diodes) and the accompanying connectivity between elements, one example of which is shown in FIG. 4. In other embodiments, detector front ends 514 include direct conversion detectors capable of energy discrimination and/or photon counting.

Referring still to FIG. 5B, each detector 512 also includes backend electronics 516 such as DAS readout chips that may include ASICs, FPGA, and the like, as is known within the industry, one example of which is shown in FIG. 4. Cooling zone 504 in one embodiment is separated by its neighboring cooling zone by a separator 518, and in other embodiments no separator is present. Nevertheless, in either embodiment each fan/opening 502 is positioned to cool a number of sets of backend electronics 516 that are positioned within cooling zone 504, thereby controlling the temperature of front end electronics 514 as well, due to the thermal contact therewith. Each fan/opening 502 is positioned to blow air into its respective cooling zone 504.

Globally, cooling air is passed within the gantry using one or more gantry fans. Referring back to FIG. 5A, gantry fans 520 are positioned on gantry 12 and are operated to extract air outwardly 522. Operation of fans 520 causes bulk or global airflow to occur within gantry 12, and the outwardly extracted air 522 causes air to inflow 524 at a gantry inlet, such as inlet 526. Bulk cooling air is thus available for local cooling of electronics within each cooling zone 504, as seen in FIG. 5B. As will be further described, electronics cooling is done within each cooling zone 504 independent of their respective fans.

Figure 6A:
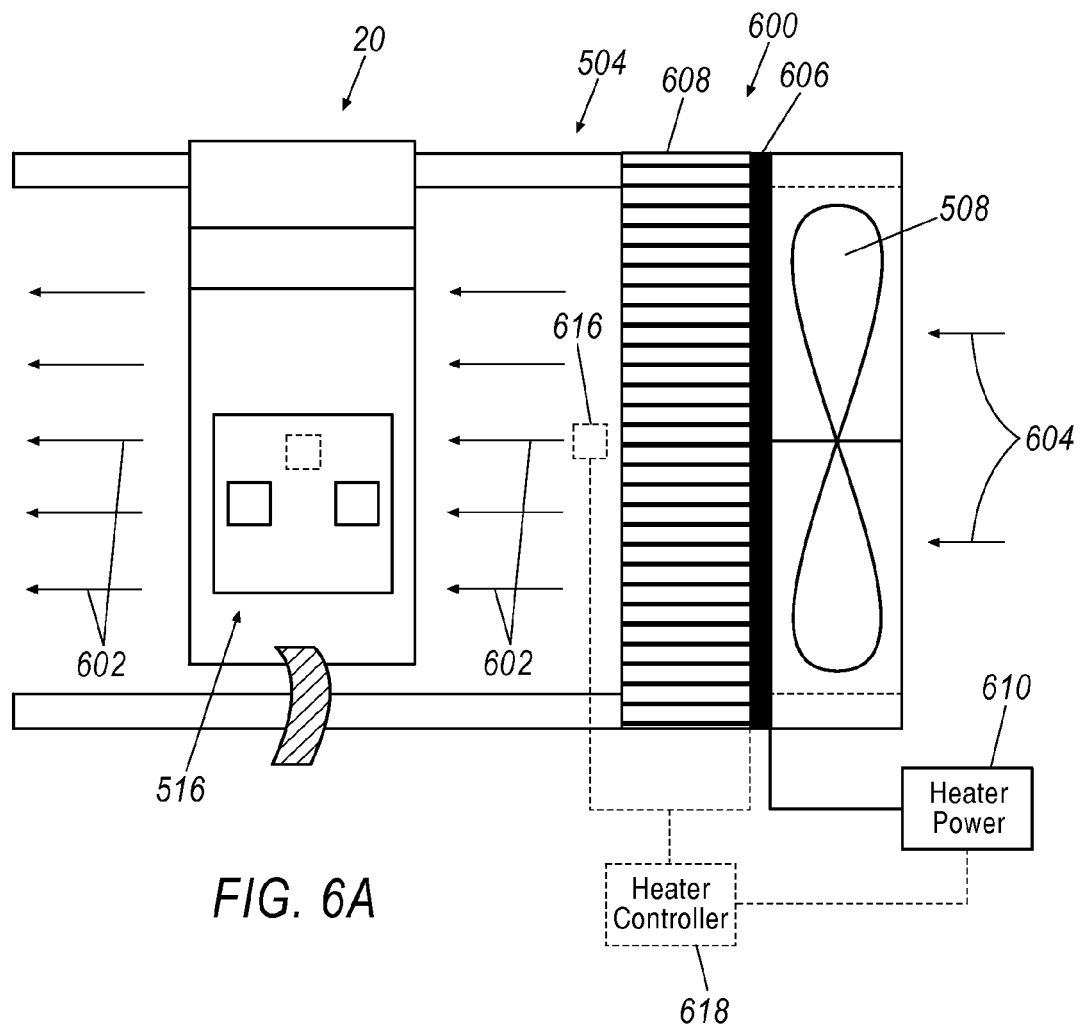
FIG. 6A is a side view of a cooling zone with one detector module in plan view.

Referring to FIG. 6A, a side view of a cooling zone is illustrated, such as cooling zone 504, with one detector module shown in plan view. Cooling zone 504 includes a heater assembly 600 that is positioned in line with its fan 508. Air blown 602 by fan 508 is input 604 and caused to pass through heater assembly 600 and be heated therewith. Heater assembly 600 includes, in one embodiment, a heating element 606 and a convection or heat transfer frame 608. In one embodiment heat transfer frame is an aluminum heat exchanger in which fins are positioned to enhance heat transfer with the air. Heating element 606 is electrically powered by a device 610 that provides power to heating element 606 which itself may be operated by a computing device, such as computer 36. Heating element 606 is in thermal contact with frame 608 such that, when air passes therethrough, the air is generally uniformly heated to a desired temperature and blown 602 across backend electronics 516.

It is desirable to calibrate and operate front end electronics 514 and back end electronics 516 with minimal temperature change between calibration and operation. That is, to avoid thermal drift and loss of calibration of detector components, it is desirable to electrically power the components of detector 20 while passing air (having a controlled and uniform temperature) over at least the back end electronics 516 during calibration. As stated, air is caused to pass through gantry 12 using gantry fans 520. As also stated, the conditions of operation of x-ray source 14 can be widely varied, depending on the number and types of scans performed, the size of the x-ray tube, etc. Further, typically x-ray source 14 is air cooled using an air-oil heat exchanger (heat exchanger not shown) that extracts the electrical power of x-ray tube via an oil coolant that is passed through the x-ray tube to an air-cooled element—dumping the x-ray tube power within gantry 12. Thus, a widely varying bulk and average temperature within gantry 12 can be experienced.

As such, heater assembly 600 causes heat to be applied to air 602 as a function of the average or bulk air temperature within gantry 12. Room air at inlet 526 may range in temperature from 18° C. to 26° C., and gantry air can range in temperature from 18° C. to greater than 35° C. Thus, it is typically desirable to calibrate and operate components of detector 20 above the maximum inner gantry temperature of 36° C. This is accomplished by heating the back end electronics 516 locally using heater assembly 600. In one example detector module 20 is heated to 38° C. Thus, regardless of inlet air temperature at 524 and regardless of the amount of power in x-ray source 14, power is applied to heater element 606 to heat air 602, to provide generally constant temperature operation of components (front and back end electronics 514, 516), enabling a generally uniform temperature of the components to be achieved during calibration and during system operation.

Figure 6B:
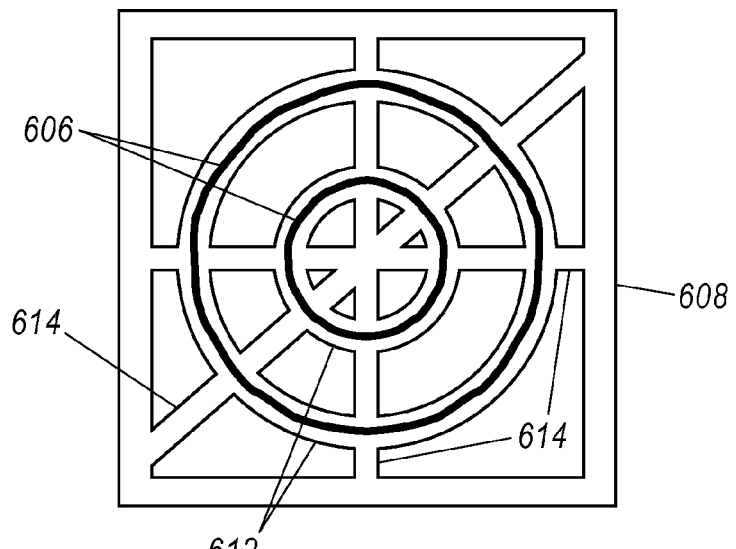
FIG. 6B is a plan view of an exemplary heater assembly of the cooling zone of FIG. 6A.

Referring to FIG. 6B, a plan view of heater assembly 600 is shown having heating element 606 and frame 608. Heating element 606 is positioned in a circular fashion in the illustrated embodiment on circular rungs 612. However, it is contemplated that any arrangement of heating element 606 is included within this disclosure, such as a rectangular or other pattern which may include other cross beams as shown. To enhance convective heat transfer, additional horizontal, vertical, and diagonal rungs 614 may be included as well. Further, although heating element 612 is shown in a circular fashion, it is contemplated that any arrangement or shape may be made of heating element 606, and any shapes of circular element 606 and rungs 614 may be employed, according to embodiments.

In one embodiment, heater assembly 600 includes a heating element that is not actively controlled by a speed of fan 508, yet temperature of air 602 within cooling zone 504 is nevertheless controlled to a desired temperature. In this embodiment heating element 606 is a Positive Temperature Coefficient (PTC) element that has self-limiting temperature characteristics. PTC elements include a very sharp increase or knee in increase of electrical resistance at a desired temperature. That is, electrical resistance is somewhat flat or mildly increasing at temperatures below the knee. Above the knee, electrical resistance increases dramatically. Thus, power is applied to the PTC is self-limiting as a function of temperature, caused by the semiconducting or Ferro-electrical properties of the PTC material, and the rise in resistance is experienced within a temperature window of 1-2° C., in one embodiment. PTC heating element 606 is not actively controlled by a temperature controller.

PTC heating elements are small ceramic stones, such as polycrystalline ceramics, that have relatively fast heating response times, and the temperature reaches a plateau once a reference temperature is reached. The PTC elements can be formed into various shapes, such as the circular shapes 612 illustrated in FIG. 6B. Thus, and as stated, when heating element 606 is fabricated of PTC material having the desired plateau or reference temperature of, for instance, 38° C., power applied thereto causes control of air temperature 602 independent of a speed of fan 508. Instead of changing the fan speed to accomplish cooling of modules 20, temperature control is accomplished by applying power to heating element(s) 606 and operating fan 508 at a constant speed.

According to another embodiment, heating element 606 are resistive heaters that are actively controlled by a controller. Referring still to FIG. 6A, in this embodiment element 616 is included and is a temperature sensor that is positioned to sense a temperature of air 602. Element 616 is electrically coupled to a heater controller 618, which is also coupled to heating element 606. In such fashion, power is applied to heating element 606 via power device 610, which is in turn controlled by controller 618. According to embodiments, controller 618 includes known controller schemes having a control loop feedback mechanism such as proportional-integral-differential (PID) control, on-off control, or proportional-integral (PI) control, as examples, that are based on a desired air temperature set point. Thus, in operation, air temperature is sensed as it exits from frame 608 and controlled via a control scheme and power is applied to the resistive heater element based on the sensed air temperature. In such fashion, air temperature within the cooling zone is controlled independent of a speed of the fan.

According to another embodiment, element 616 is a thermostat that is configured to cycle power to resistive heating element 606 based on the sensed air temperature. In this embodiment, thermostat 616 is caused to open and close as a temperature set point is crossed during heating and cooling cycles. That is, air temperature 602 is caused to rise and fall during on-off operation of heating element 606. The amount of rise and fall is established, in one example, in thermostat 616 and based on trigger temperatures above and below the set point. In such fashion, air temperature within the cooling zone is controlled independent of a speed of the fan.

As such, detector electronics 514, 516 are cooled by blowing air 602 with a fan 508 into cooling zone 504 in which electronics 514 are positioned, and the temperature of electronics 514, 516 is controlled without altering a speed of fan 508. Further, although detector assembly 20 of FIG. 4 is described with respect to the cooling scenarios disclosed herein, it is contemplated that any detector design in which the electronics are thermally coupled to the sensor may be included herein. For instance, detector front end electronics (i.e., scintillator/diode or direct conversion device) may be positioned on a rail such as a metal frame, and a cooling member or heat sink may be positioned within the cooling plenum, wherein a temperature of the heat sink is controlled by the embodiments disclosed. In one example, the backend electronics (A/D ASICs, FPGA, etc.) may be positioned on the rail or metal frame that itself forms the plenum, in which case the electronics are considered to be within the plenum or cooling zone.

Figure 7:
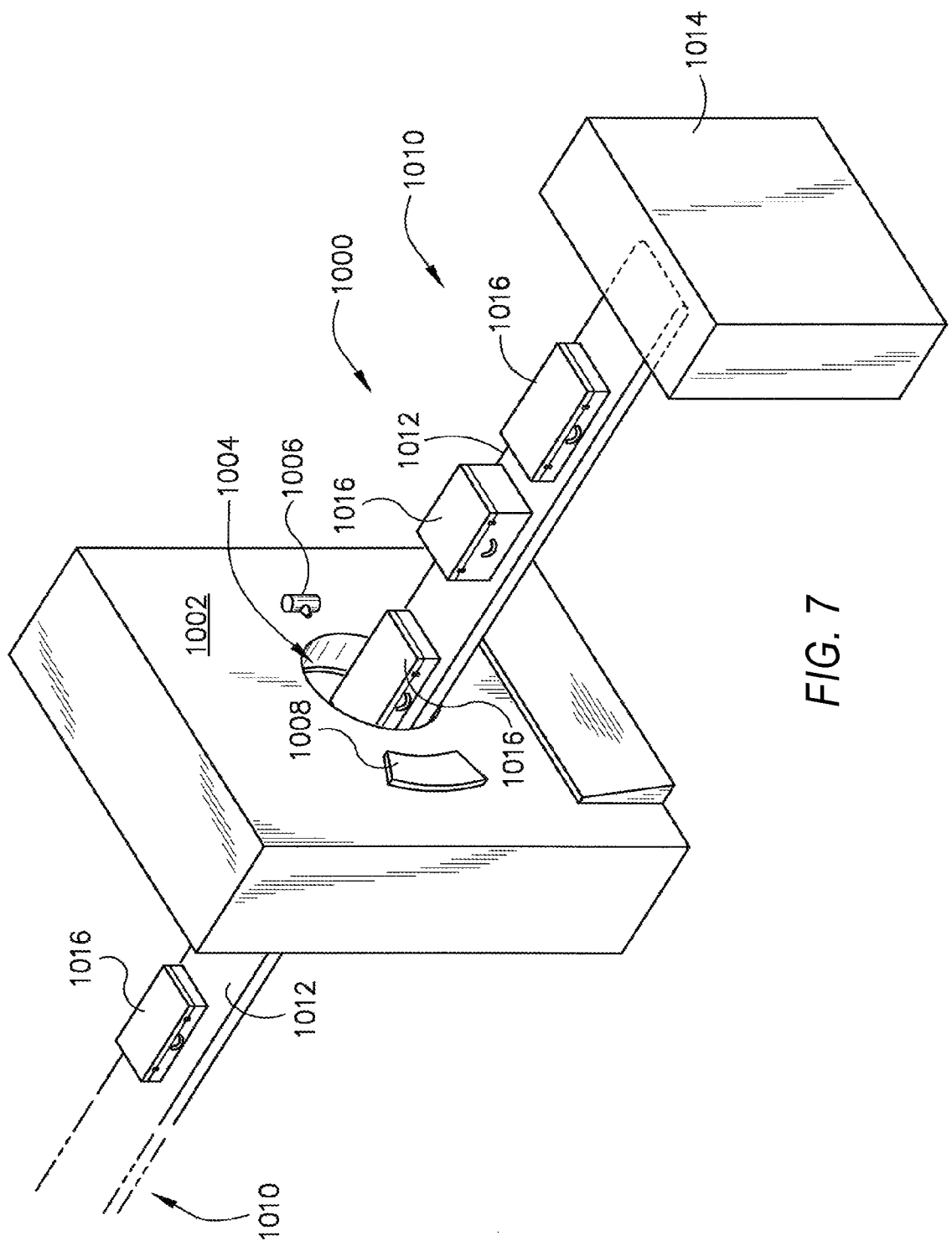
FIG. 7 is a pictorial view of a CT system for use with a non-invasive package inspection system that incorporates embodiments of the disclosed subject matter.

Referring now to FIG. 7, there is shown a package/baggage inspection system 1000 that can use the image acquisition and reconstructions techniques according to embodiments disclosed and which includes a rotatable gantry 1002 having an opening 1004 therein through which packages or pieces of baggage may pass. The rotatable gantry 1002 houses one or more x-ray energy sources 1006 as well as a detector assembly 1008 having scintillator arrays comprised of scintillator cells. A conveyor system 1010 is also provided and includes a conveyor belt 1012 supported by structure 1014 to automatically and continuously pass packages or baggage pieces 1016 through opening 1004 to be scanned. Objects 1016 are passed through opening 1004 by conveyor belt 1012, imaging data is then acquired, and the conveyor belt 1012 removes the packages 1016 from opening 1004 in a controlled and continuous manner. As a result, postal inspectors, baggage handlers, and other security personnel may non-invasively inspect the contents of packages 1016 for explosives, knives, guns, contraband, etc.

An implementation of system 10 and/or 1000 in an example comprises a plurality of components such as one or more of electronic components, hardware components, and/or computer software components. A number of such components can be combined or divided in an implementation of the system 10 and/or 1000. An exemplary component of an implementation of the system 10 and/or 1000 employs and/or comprises a set and/or series of computer instructions written in or implemented with any of a number of programming languages, as will be appreciated by those skilled in the art. An implementation of system 10 and/or 1000 in an example comprises any (e.g., horizontal, oblique, or vertical) orientation, with the description and figures herein illustrating an exemplary orientation of an implementation of the system 10 and/or 1000, for explanatory purposes.

An implementation of system 10 and/or system 1000 in an example employs one or more computer readable signal bearing media. A computer-readable signal-bearing medium in an example stores software, firmware and/or assembly language for performing one or more portions of one or more implementations. An example of a computer-readable signal-bearing medium for an implementation of the system 10 and/or the system 1000 comprises the recordable data storage medium of the image reconstructor 34, and/or mass storage device 38 of computer 36. A computer-readable signal-bearing medium for an implementation of the system 10 and/or the system 1000 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 1000, for instance, one or more of a telephone network, a local area network ("LAN"), a wide area network ("WAN"), the Internet, and/or a wireless network.

According to one embodiment, a CT system includes a rotatable gantry having an opening for receiving an object to be scanned, an x-ray source configured to project x-rays through the opening, and a detector assembly positioned to receive the x-rays. The detector assembly includes a plurality of readout chips positioned within a cooling zone and configured to receive electrical signals from a plurality of diode arrays, and a fan positioned to blow air into the cooling zone. An air temperature within the cooling zone is controlled independent of a speed of the fan.

According to another embodiment, a method of cooling detector electronics within an imaging gantry includes blowing air with a fan into a cooling zone in which the detector electronics are positioned, and controlling a temperature of the detector electronics without altering a speed of the fan.

According to yet another embodiment, a detector assembly is positionable to receive x-rays from an x-ray tube within an imaging system. The detector assembly includes a cooling zone having a plurality of readout chips positioned therein, the readout chips configured to receive electrical signals from a plurality of diode arrays, and a fan coupled to the detector assembly and positioned to blow air into the cooling zone. An air temperature within the cooling zone is controlled independent of a speed of the fan.

A technical contribution for the disclosed method and apparatus is that it provides for a computer-implemented apparatus and method for temperature control in a detector for a computed tomography (CT) gantry.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications).

While the disclosed subject matter has been described in detail in connection with only a limited number of embodiments, it should be readily understood that the disclosed subject matter is not limited to such disclosed embodiments. Rather, that disclosed can be modified to incorporate any number of variations, alterations, substitutions or equivalent arrangements not heretofore described, but which are commensurate with the spirit and scope of the disclosed subject matter. Furthermore, while single energy and dual-energy techniques are discussed above, that disclosed encompasses approaches with more than two energies. Additionally, while various embodiments of the disclosed subject matter have been described, it is to be understood that disclosed aspects may include only some of the described embodiments. Accordingly, that disclosed is not to be seen as limited by the foregoing description, but is only limited by the scope of the appended claims.

What is claimed is:

1. A CT system, comprising:
    a gantry having an opening for receiving an object to be scanned;
    an x-ray source, attached to the gantry, to project x-rays through the opening; and
    a detector assembly, attached to the gantry, to receive the x-rays, the detector assembly comprising:
        a plurality of readout chips positioned within a cooling zone and configured to receive electrical signals from a plurality of diode arrays;
        a fan positioned to blow air into the cooling zone; and
        a heater assembly positioned in line with the fan such the air blown from the fan is heated by the heater assembly.

2. The CT system of claim 1, wherein the heater assembly comprises a heating element that is not actively controlled by a temperature controller.

3. The CT system of claim 2, wherein the heating element is a positive temperature control (PTC) heating element.

4. The CT system of claim 1, wherein the heater includes a resistive heating element that is actively controlled by a thermal controller.

5. The CT system of claim 4, wherein the thermal controller includes:
    a temperature sensor positioned to sense the air temperature; and
    a control loop feedback mechanism to provide power to the resistive heating element based on the sensed air temperature.

6. The CT system of claim 5, wherein the control loop feedback mechanism includes at least one of a proportional-integral-differential (PID) controller, an on-off controller, and a proportional-integral (PI) controller that are based on a desired temperature set point for the air temperature.

7. The CT system of claim 5, wherein the control loop feedback mechanism is a thermostat that cycles power to the resistive heating element based on the sensed air temperature.

8. The CT system of claim 1, wherein the CT system is one of a medical imaging system and a baggage scanner.

9. A detector assembly positionable to receive x-rays from an x-ray source within an imaging system, the detector assembly comprising:
    a cooling zone having a plurality of readout chips positioned therein, the readout chips configured to receive electrical signals from a plurality of diode arrays;
    a fan positioned to blow air into the cooling zone; and
    a heater assembly positioned in line with the fan such the air blown from the fan is heated by the heater assembly.

10. The detector assembly of claim 9, wherein the heater assembly comprises a positive temperature control (PTC) heating element that is not actively controlled by a temperature controller.

11. The detector assembly of claim 9, wherein the heater assembly includes a resistive heating element that is actively controlled by a thermal controller.

12. The detector assembly of claim 11, wherein the thermal controller includes:
- a temperature sensor positioned to sense the air temperature; and
- a control loop feedback mechanism to provide power to the resistive heating element based on the sensed air temperature.

* * * * *